United States Patent [19]

Thompson

[11] Patent Number: 5,074,987
[45] Date of Patent: Dec. 24, 1991

[54] ONLINE ENERGY FLOW MEASURING DEVICE AND METHOD FOR NATURAL GAS

[75] Inventor: William L. Thompson, Montville, Ohio

[73] Assignee: Elsag International B.V.

[21] Appl. No.: 469,869

[22] Filed: Jan. 24, 1990

[51] Int. Cl.$^5$ .......................................... G01N 27/46
[52] U.S. Cl. .................................. 204/410; 204/406; 204/153.18
[58] Field of Search .................... 204/153.18, 410, 406

[56] References Cited

U.S. PATENT DOCUMENTS

| | | | |
|---|---|---|---|
| 3,514,377 | 5/1970 | Spacil et al. | 204/153.18 |
| 3,981,785 | 9/1976 | Sandler | 204/410 |
| 4,841,934 | 6/1989 | Logothetis et al. | 123/440 |

OTHER PUBLICATIONS

Griffis, C. H. et al.-"Development of an Accurate Energy Flowmeter", Gas Quality, ed by van Rossum, G. J., Elsevier Science Publishers, Amsterdam, Apr. 22-25, 1986, pp. 121-127.
Heyne, L., "Some Properties and Applications of Zirconia-Based Solid-Electrolyte Cells", Proc. Interdisp Symposium, 1974, pp. 65-88.
Vizethum, F., Bauer G., and Tomandl, G., "Computer-Control of Oxygen Partial Pressure", Science and Technology of Zirconia II (Proceedings of the Second International Conference), date unknown, pp. 631-635.
Haaland, D. M., "Internal-Reference Solid-Electrolyte Oxygen Sensor", Analytical Chemistry, vol. 49, No. 12, Oct. 1977, pp. 1813-1817.
Speidel, R. and Weidlich, E-R., "A Solid State Oxygen Source for UHV", Vacuum, No. 2, 1988, pp. 88-92.
Wilde, D. and Arcara, S., "Modern Energy Flow Measurements", Advances in Instrumentation, Proceedings of the ISA International Conference and Exhibit, 1984, Oct. 22-25, pp. 1345-1349.
Logothetis, E. M. Vassell, W. C., Hetrick, R. E., and Kaiser, W. J., "A High-Sensitivity Sensor for the Measurement of Combustable Gas Mixtures", Transducers '85: 1985 International Conference on Solid State Sensors and Activators, IEEE 1985, pp. 330-332.
Takeuchi, Takashi, "Oxygen Sensors", Sensors and Actuators, vol. 14, 1988, pp. 109-124.
Handbook of Physics, Second Edition, ed by Condon, E. U., and Odishaw, H., McGraw-Hill, New York, 1967, pp. 4-147 to 4-148.
Logothetis, E. M. and Metrick, R. E., "High-Temperature Oxygen Sensors Based on Oxygen Pumping", Chapter 8 in Fundamentals and Applications of Chemical Sensors, the American Chemical Society, 1986, pp. 136-154.
Table 1-"Combustion Constants", p. 6-2, from Steam: Its Generation and Use, 38th Ed., by the Babcock & Wilcox Company, New York, 1975, p. 6-2.

Primary Examiner—John Niebling
Assistant Examiner—Arun S. Phasge
Attorney, Agent, or Firm—Vytas R. Matas; Robert J. Edwards

[57] ABSTRACT

A method and device for measuring energy in fuel gas comprises a solid electrolyte oxygen pump for generating an amount of oxygen in response to current being supplied to the pump. A sample of the gas is mixed with the oxygen from the pump to produce a mixture which is subjected to complete combustion in a catalytic combustor. An oxygen sensor is connected to the catalytic combustor for measuring excess oxygen in the exhaust gas from the combustor. A signal from the oxygen signal is compared to a known and desired amount of excess oxygen in the exhaust gas. If there is too much or too little oxygen inthe exhaust gas, a feedback signal is used to adjust the amount of current being supplied to the oxygen pump until the actual amount of excess oxygen is equal to the selected amount of excess oxygen. The selected amount of excess oxygen is indicative of complete combustion of the sample mixture. With the excess oxygen equaling the desired oxygen in the exhaust gas, the amount of current being supplied to the pump is used to calculate the energy in the fuel sample.

7 Claims, 3 Drawing Sheets

ONLINE ENERGY FLOW MEASURING DEVICE AND METHOD FOR NATURAL GAS

FIELD AND BACKGROUND OF THE INVENTION

The present invention relates in general to electrochemical measuring techniques, and in particular to a new and useful method and device for measuring the energy content of combustion gases.

Energy flow is the important parameter when natural gas is being sold or purchased. The customer is interested in how much heat energy he can get from the gas he is purchasing. The seller typically has a contractual agreement to supply a known minimum energy content with each cubic foot of gas. In order to meet this content the producer typically provides a higher value to compensate for errors in the measurement system. Several parameters or variables must be measured in the present state of measurement technology. Each measurement has its own error contribution. Energy flow is currently not measured directly but is computed by taking an off-line sample to a calorimeter or gas chromatograph for a specific energy measurement. This is used in conjunction with volume flow, temperature, pressure, etc., to calculate an energy flow. This is an involved process, requiring large, expensive instrumentation. This implementation utilizes a tapped fraction of the total flow. This fraction is introduced into a combustion system along with a controlled amount of air. A stoichiometric combustion sensor monitors the output. Its output is used by an element which adjusts the air delivery system. The combustion air flow is measured and the energy flow is calculated from the air flow and the calibration of the split-off fraction or ratio. See Griffis, C. H., et al. "Development of an Accurate Energy Flowmeter", *Gas Quality*, ed by van Rossum, G. J., Elsevier Science Publishers, Amsterdam, Apr. 22-25, 1986, pages 121-127.

On pages 77, 78 of Heyne, L., "Some Properties and Applications of Zirconia-based Solid-Electrolyte Cells", *Proc Interdisp Symposium*, 1974, pages 65-88, the use of a combination of an oxygen pump and sensor as an analyzer for combustibles gases is discussed. This depends on combustion at the pump cell. The oxygen introduced is regulated so that it is just what is needed from complete combustion of the combustible gases present. The current or charge used to pump oxygen is thus a measure of the combustible gases.

An apparatus is described in Vizethum, F., Bauer, G., and Tomandl, G., "Computer-Control of Oxygen Partial Pressure", *Science and Technology of Zirconia II* (*Proceedings of the Second International Conference*, pages 631 to 635, in which oxygen partial pressure is controlled by a zirconia solid electrolyte cell and an oxygen sensor of the same material. This partial pressure control is used in a gas titration system.

Haaland, D. M., "Internal-Reference Solid-Electrolyte Oxygen Sensor", *Analytical Chemistry*, Vol. 49, No. 12, October 1977, pages 1813-1817, discusses an electrochemical pumping oxygen sensor with a monitor section and a pumping section. This type essentially uses a small leak from the gas being measured and a pump to evacuate all the oxygen that enters the cell. A measure of the pumping current gives a measure of the oxygen that leaks in and thus a measure of the oxygen in the stream being measured. This type was developed for use in automotive applications.

U.S. Pat. No. 4,841,934 discusses using an oxygen pumping device in conjunction with an oxygen sensor to control the air-fuel ratio of an engine. This uses a combination of an oxygen pumping device and an oxygen sensing device, a double $ZrO_2$ configuration. This essentially modifies the oxygen concentration operating region of the sensor to improve the signal characteristics of the sensor at its desired operating point. This essentially provides the high sensitivity available at stoichiometry only for other mixtures or concentrations.

Solid oxygen sources are available. These may be metal oxides where the oxygen is liberated upon heating the material. Speidel, R., and Weidlich, E-R, "A solid state oxygen source for UHV", *Vacuum*, no. 2, 1988, pages 89 to 92, discuss a device for employing CuO as the solid source. Here a constant partial pressure of oxygen is generated by applying heat to the material, causing the material to decompose. The partial pressure is a function of the heat applied to the material. This thus liberates a controlled, small amount of oxygen. This in turn is a self-contained source for the oxygen pump to use as it delivers a controlled, known amount of oxygen to the flow stream inside the energy sensor arrangement.

SUMMARY OF THE INVENTION

An on-line, real time single sensor method is preferable over the one that uses a number of measurements with one or more of the measurements being made off line. The indirect method described above requires that many parameters by measured. Each measurement has an error associated with it which contributes to the error level of the overall measurement system (Wilde, D., and Arcara, S., "Modern Energy Flow Measurements", *Advances in Instrumentation, Proceedings of the ISA International Conference and Exhibit*, 1984, Oct. 22-25, pages 1345-1349). The present invention does not use the large and expensive equipment required in the above mentioned references, but rather is a more direct measurement technique. The actual flow of energy in a controlled fraction of the total flow is measured by the invention, as contrasted to measuring several flow parameters, such as volume flow, pressure, temperature, etc., and calculating the energy flow as in the prior art.

The operation in a single element mode such as a fuel cell, results in electrode problems caused by the complete depletion of oxygen at the surface of the electrolyte (Logothetis, E. M., Vassell, W. C., Hetrick, R. E., and Kaiser, W. J., "A High-Sensitivity Sensor for the Measurement of Combustible Gas Mixtures", *Transducers '85: 1985 International Conference on Solid State Sensors and Actuators*, IEEE, 1985, pages 330-332). Also fuel cells operate at less than 100% efficiency. To use them requires multiple stages to get to a point where all of the combustible material is burned and measured. One implementation utilizes a two element configuration with a pump and a sensor (see Heyne, at pages 77, 78). This implementation adds a catalytic converter to the system to insure that all of the material is combusted. This insures a high accuracy measurement of the gas being combusted by eliminating the error term associated with incomplete combustion.

When operated at the stoichiometric point, a zirconia sensor has a high accuracy and reliability in practical use (Takeuchi, Takashi, "Oxygen Sensors", *Sensors and Actuators*, Vol. 14, 1988, pages 109-124). There is some combustion in the oxygen pump region of the device. However, the completeness of combustion in the pumping area or in the fuel cell operation is not 100% a priori. Use of a catalytic converter section assures 100% combustion and the following oxygen sensor is operated in a highly accurate region. This configuration combines to provide a high accuracy in the operation.

Thus, according to the present invention, a continuous, real-time portion or sample of the total flow of combustion gas is passed through the sensing system. This sample has a predetermined, known ratio to the total flow and has the same temperature, pressure and other parameters as the flow being measured. The sample is mixed with a controlled amount of oxygen and introduced into a catalytic combustion device so that complete combustion occurs. The output exhaust gas of the combustion stage or device is measured to determine if the oxygen-gas mixture supplied to the combustion stage was as desired, that is either stoichiometric or with a preset valve of excess oxygen, dependent on the mode of operation of the system.

If the mixture was not as desired, the oxygen introduced into the sample flow is changed so that the desired mixture is obtained. The oxygen is introduced into the sample flow using a solid-electrolyte, typically zirconia, oxygen pump. The oxygen being pumped is directly related to the current passed through the cell. This is known as the Faraday effect—in an electrolyte, the quantity of electricity that flows is directly related to the quantity of electronic charge on the ions entering into the reaction at the electrodes (*Handbook of Physics*, Second Edition, ed by Condon, E. U., and Odishaw, H., McGraw-Hill, New York, 1967, page 4-147 to 4-148). The current in the electrochemical pump thus is directly related to the oxygen being pumped plus a small leakage term. Faraday efficiency—one oxygen ion transported per two electrons of current flow—is very close to unity, when the pumping cell and the measuring cell do not share common electrodes (Logothetis, E. M., and Hetrick, R. E., "High-Temperature Oxygen sensors based on Oxygen Pumping", Chapter 8 in *Fundamentals and Applications of Chemical Sensors*, The American Chemical Society, 1986, pages 136-154). The separate electrodes eliminate the effect of polarization, at the electrodes and at grain boundaries, on the characteristics of the cell. The current in the cell flows primarily by the transport of the oxygen ions in the electrolyte. There is some leakage or resistive current flow but this is very low.

A controlled amount of oxygen is supplied to get complete combustion. The energy content of the gas so combusted is directly related to the quantity of oxygen required for combustion. The oxygen required varies linearly with flow rate and with calorific content of the gas. The current through the oxygen pump is directly related to the oxygen pumped. Thus the current is directly related to the BTU flow through the device. In instances where the flow through the device is a constant sub-multiple of the flow in a large conduit, as a gas pipeline, the output of the sensor gives a measure of the energy flow in the large conduit.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
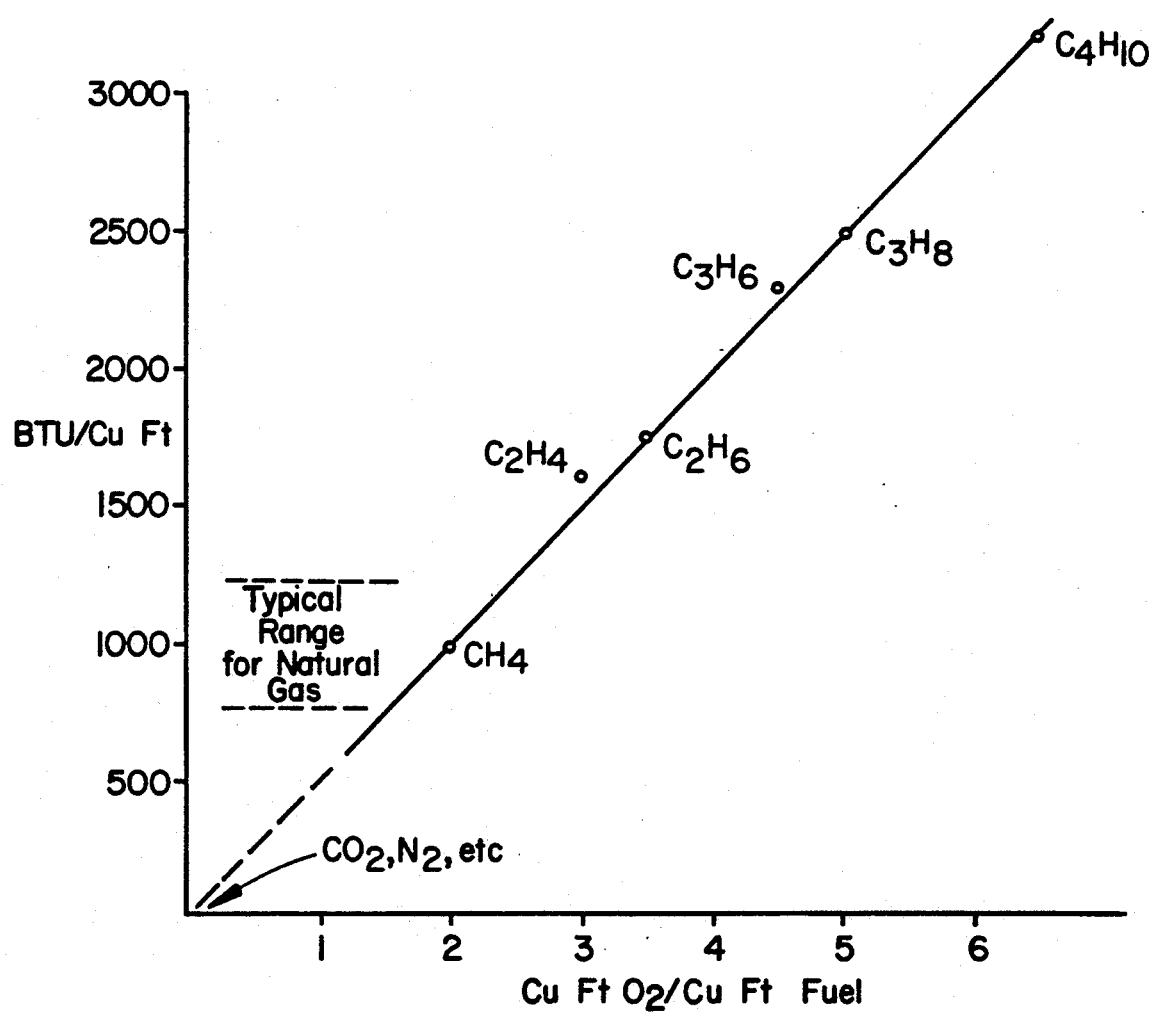
FIG. 1 is a graph plotting the relationship between oxygen required for a stoichiometric combustion of combustible compounds commonly found in natural gas, any energy or heat content of the combustion gases, with BTU/Cu Ft$_3$ values at 60° F. and 30 inches of mercury, wet.

Referring to the drawings in particular, FIG. 1 is a plot of the BTU content of natural gas plotted against the oxygen required to completely combust its constituents (Steam, 38th ed, by the Babcock and Wilcox Company, New York, 1975 page 6-2). Thus the oxygen required to completely combust a given volume of the majority of mixtures of natural gas is related to the BTU content of that same volume of the gas.

Figure 2:
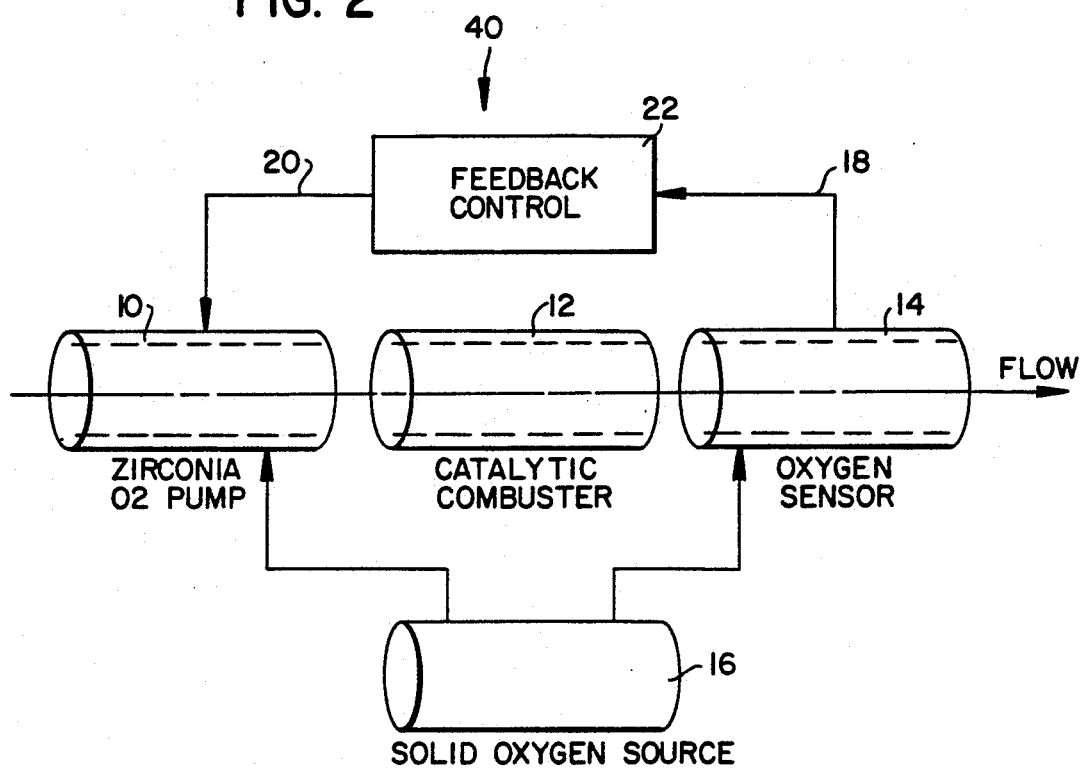
FIG. 2 is an exploded schematic view of a device of the present invention utilized to practice the method of the present invention.

This approach is very sensitive to flow and energy and insensitive to variations in temperature, gas density, and moisture. FIG. 2 functionally displays the implementation. Although the figure shows a cylindrical geometry for instructional purposes, the actual geometries would include a long narrow cylindrical section, honeycombed cross sections, sections with parallel sides and very small separations, etc. all of which serve to maximize the area presented to the flow in order to maximize the efficiency of the cell. The factor of importance is that sufficient oxygen is introduced into the gas flow to provide for complete combustion.

The quantity of oxygen is varied from stoichiometry to excess oxygen to verify operability of the device. This variation is applied periodically to insure that the device is operating properly. A variable fraction of the oxygen can be pumped to give varying levels of combustion rather than stoichiometric mixtures. Changing the levels can be used to check performance by determining if the output oxygen indication increases with a call for a higher level of oxygen to be pumped. The sensor has a very high gain at the stoichiometric combustion point and a slight change in the oxygen level causes a large change in output when it is functioning properly. This test serves to verify the operation of the oxygen pump and the oxygen sensor. It also indicates whether combustion is taking place at the catalytic combustor since the oxygen sensor indicates no excess oxygen for a level of oxygen being pumped into the gas stream.

The measuring assembly 40 of the invention is shown schematically in FIG. 2. The flow is from left to right. The geometry in practice has small area opening relative to the cross sectional area of the interior of the device. This is to provide a large area which is exposed to the flow for oxygen pumping and for combustion in order to insure that the combustion process is complete. This is necessary to the accuracy of the measurement.

Gas flowing from left to right enters the first component of the system which is a device capable of providing a controllable source of oxygen. This is a miniature fuel cell 10 using a solid electrolyte such as a stabilized zirconia. It produces or pumps oxygen to its interior directly related to the electron current which is passed through it. The oxygen it introduces into the flow will mix with the gases in the flow stream. The mixture is then combusted in a catalytic combustor 12, the second element of the arrangement. The output of the catalytic combustor will be a mixture of carbon dioxide, water vapor, oxygen and possibly some unburned combustible gases. These gases are then passed through the third member of the arrangement, a zirconia oxygen sensor 14. The reference oxygen for this sensor is supplied either from atmosphere or from a solid sealed oxygen source 16. The voltage output 18 of the oxygen sensor makes a large, sudden increase when going from the condition of some oxygen in the sensing volume to the condition where all of the oxygen is removed from the sample. The point where this occurs is independent of the reference pressure unless the reference is very low (see the Heyne reference at page 84). Thus the oxygen source is not critical in the accuracy of the control when the system is operated at stoichiometric mixtures. The oxygen pump 10, catalytic converter 12, and oxygen sensor 14 are operated in the range of 600° to 700° C. The solid oxygen source 16 could be operated by the same heater system that controls the temperature of the other parts of the system. The oxygen source for the oxygen pump 10, the first member of the invention, is likewise supplied typically either from the atmosphere, or from the solid source 16 as shown in FIG. 2 (see the Speidel et al. reference). The output 18 of the oxygen sensor 14 is used to control the current 20 supplied to the oxygen pump 10. The control circuit 22 of the invention, compares the output of the oxygen sensor 14 with a setpoint value and either increases or decreases the current 20 accordingly. This causes the amount of oxygen being pumped to change as the current changes. The control loop operates either at a stoichiometric mixture or one which is slightly oxygen rich either increasing or decreasing the flow of oxygen so that the oxygen measured by the sensor is held constant. The current through the pump section is a measure of the oxygen needed for total combustion of the gas flowing through the sensor arrangement.

The current used to control the oxygen pump is quantitatively related to the oxygen required for complete combustion. This is converted to a digital value and used in a calculation of energy value, using constants from the flow ratio and the data plotted in FIG. 1, etc.

Figure 3:
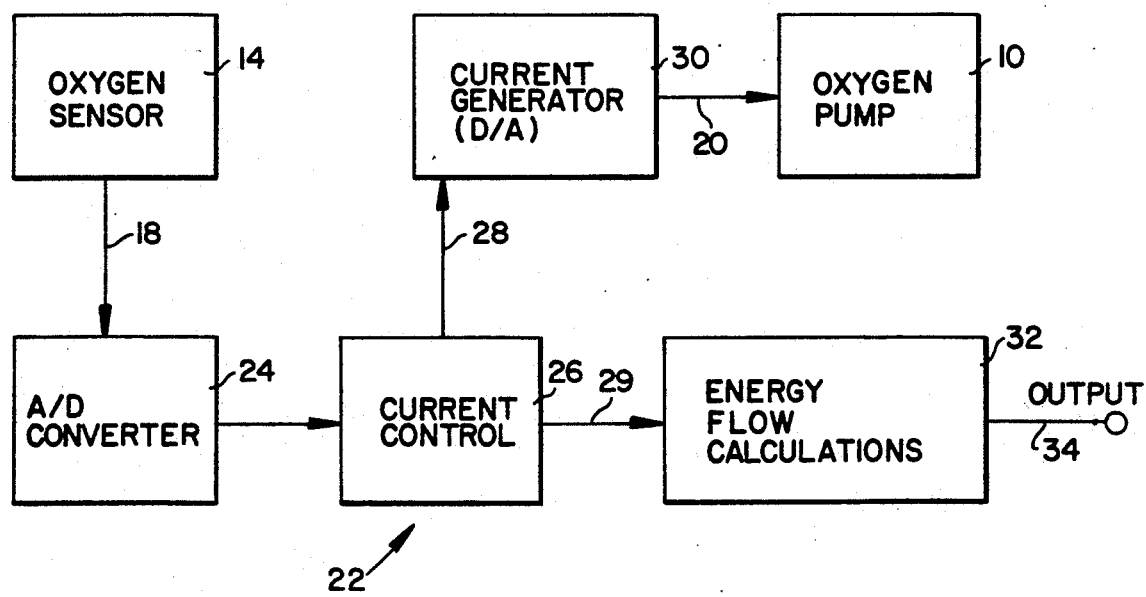
FIG. 3 is a block diagram showing the electronic components in an electronic arrangement used to practice the present invention.

FIG. 3 diagrammatically shows the electronic system for the energy flowmeter of the invention except for the heater control for maintaining the parts at the necessary temperature. The oxygen sensor's output 18 is a voltage. This voltage is converted to a digital value by an A/D converter 24. This digital value is compared to a setpoint by a current control unit 26. The output 28 of this current control unit 26 operates a current generator 30 which in turn supplies a drive current 20 to the oxygen pump 10. When the oxygen signal is lower than the setpoint or desired value, the current generator 30 is instructed to increase its output by a small amount. Conversely, when the oxygen signal is above the setpoint, the current generator 30 is instructed to decrease the current by a small amount. This action continually repeats with a time interval between actions and an amount of change selected together to keep the control loop stable.

The current generator 30 accepts a digital signal at 28 and outputs a current at 20. This is a current-output D/A circuit. The voltage compliance of the output of this circuit is limited to $+/-$ 2.5 volts (see the Heyne reference at page 71) to protect the sensor. The digital output at 29 of the current control unit is also used for the energy flow calculation at 32. This unit 32, as well as the other control circuitry, is microprocessor-based with the constants necessary for its calculations stored in its memory. The calculated output 34 of unit 32 gives the energy measurement of the invention.

The sensor assembly 40, including oxygen pump 10, catalytic combustor 12, oxygen sensor 14, solid oxygen source 16, heater (not shown), etc., is mounted in a flow conduit 42 to obtain a measure of the total energy flow in the conduit of sizes which may range from a few inches to one with a diameter of 30 inches or larger.

Figure 4:
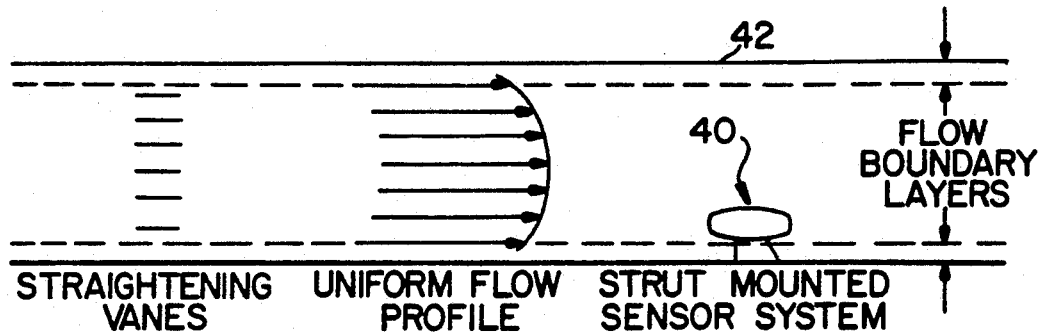
FIG. 4 shows the use of a device according to the present invention utilized in-situ for directly measuring energy available in a flow of fuel gas.
Figure 5:
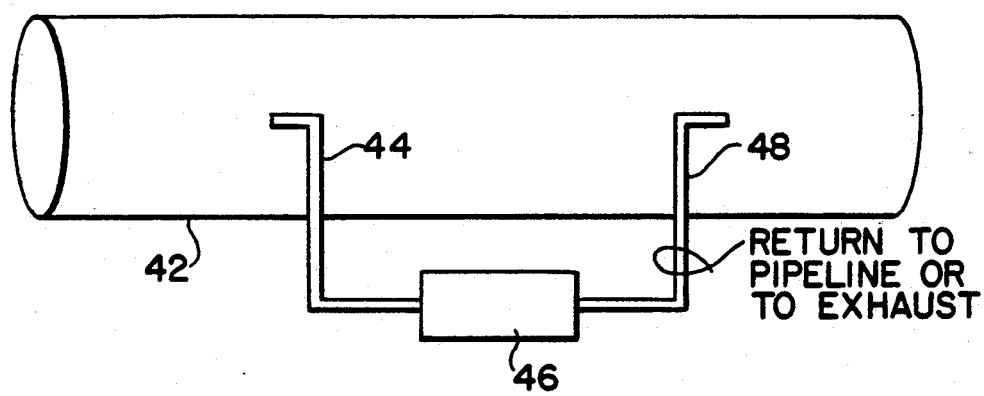
FIG. 5 illustrates an embodiment of the present invention which is positioned outside of the main flow of fuel gas.

One mounting arrangement uses a package mounted on the inside wall of the conduit using a strut assembly as shown in FIG. 4. An alternate implementation shown in FIG. 5 uses a flow sampling technique in which a small sample of the stream is routed at 44 out of the primary conduit 42 and to the energy flow sensor 46 which is similar to assembly 40. The flow sensor gas stream output is exhausted back into the primary flow at 48 so that there is no net pressure drop through the sensing assembly. Isokinetic sampling is preferred to maintain the accuracy of the ratio of flow between the sample and the main flow.

Figure 6:
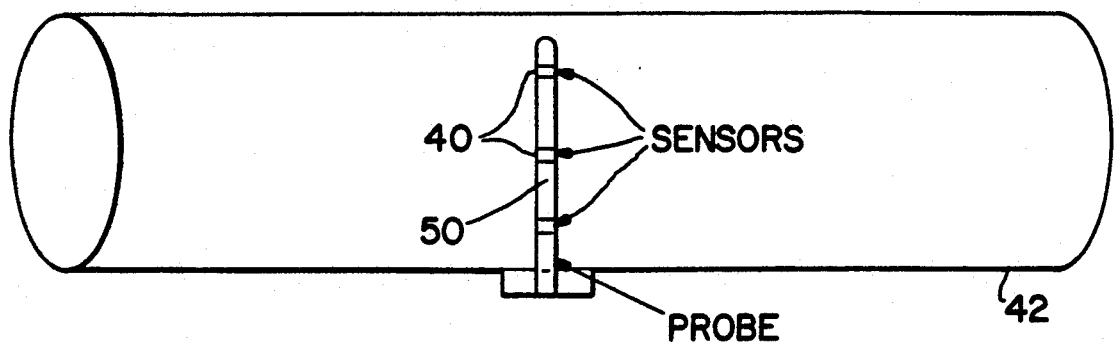
FIG. 6 is a schematic illustration of another arrangement for utilizing the present invention.

Another arrangement is to mount the sensor 40 in a probe 50 which is inserted into the flow conduit 42. A single energy flow metering device can be mounted in the probe and inserted into the conduit, or an array of them may be mounted in the probe, as shown in FIG. 6, to measure across a flow conduit in the case of a flow that had a non-uniform cross-section.

While the specific embodiments of the invention have been shown and described in detail to illustrate the application of the principles of the invention, it will be understood that the invention may be embodied otherwise without departing from such principles.

What is claimed is:

1. A device for measuring the energy in a fuel gas, comprising:
   a solid-electrolyte oxygen pump for receiving a sample of the gas and for generating an actual amount of combustion oxygen when the pump is powered by an amount of current which is proportional to the actual amount of combustion oxygen;
   a catalytic combustor connected to the pump for receiving a mixture of the same plus the actual amount of combustion oxygen for combustion of the sample to form an exhaust gas having an actual amount of exhaust oxygen therein;
   an oxygen sensor connected to the combustor for sensing the actual amount of exhaust oxygen in the exhaust gas;

a solid oxygen source connected to the pump and to the oxygen sensor for supplying calibrating oxygen to the pump and to the oxygen sensor; and a feed back control unit connected between the oxygen sensor and the pump for sensing the actual amount of exhaust oxygen in the exhaust gas and generating the amount of current based on the actual amount of exhaust oxygen sensed, the control unit comparing the actual amount of exhaust oxygen to a selected amount of exhaust oxygen which is indicative of complete combustion in the combustor and adjusting the amount of current so that the actual amount of exhaust oxygen approximately equals the selected amount of exhaust oxygen, the control unit including calculating means for calculating the amount of energy in the fuel gas as a function of the actual amount of current being supplied to the pump.

2. A device according to claim 1 wherein the pump comprises a zirconia pump.

3. A device according to claim 1 wherein the oxygen sensor produces an analog signal which is proportional to the actual amount of oxygen in the exhaust gas, the control unit including an A/D converter connected to the oxygen sensor for producing a digital signal, current control means connected to the A/D converter for producing digital current signals which are proportional to the amount of oxygen, a D/A current generator connected to the current control means for generating the actual current for supply to the oxygen pump, and calculator means connected to the current control means for calculating an energy signal which represents a measurement of the energy in the gas, the energy signal being calculated as a function of the digital signal from the current control means.

4. A device according to claim 1, further comprising a strut assembly for mounting the device on an inside wall of a conduit through which the fuel gas flows.

5. A device according to claim 1 further including isokinetic sampling means for routing the sample of the fuel gas out of a primary conduit through which the fuel gas flows to the device and means for exhausting the exhaust gas from the device back into the conduit.

6. A device according to claim 1, further including a probe for mounting the device therein, said probe being inserted into a flow conduit through which the fuel gas flows.

7. A device according to claim 6, further including an array of devices mounted in the probe to measure across a flow conduit in a case of a flow that has a non-uniform cross-section.

* * * * *